United States Patent [19]

Schacht et al.

[11] 4,168,312
[45] Sep. 18, 1979

[54] QUINOLONE DERIVATIVES

[75] Inventors: Erich Schacht, Darmstadt; Hans Dahm, Dormagen; Reinhard Lissner, Darmstadt, all of Fed. Rep. of Germany

[73] Assignee: Merck Patent Gesellschaft mit beschrankter Haftung, Darmstadt, Fed. Rep. of Germany

[21] Appl. No.: 849,585

[22] Filed: Nov. 8, 1977

[30] Foreign Application Priority Data

Nov. 12, 1976 [DE] Fed. Rep. of Germany ....... 2651581

[51] Int. Cl.$^2$ .................... A61K 31/47; C07D 215/22
[52] U.S. Cl. ...................... 424/258; 546/155; 546/157; 562/454; 562/456; 562/457
[58] Field of Search ................. 260/287 K; 424/258; 546/155

[56] References Cited

U.S. PATENT DOCUMENTS

| | | | |
|---|---|---|---|
| 2,962,523 | 11/1960 | Godt | 260/287 K |
| 3,635,985 | 1/1972 | Nishimura et al. | 260/287 K |
| 4,065,456 | 12/1977 | Nakagawa et al. | 424/258 |
| 4,065,457 | 12/1977 | Buckel et al. | 424/258 |

OTHER PUBLICATIONS

Ziegler et al., "Justig Liebigs Ann. Chem.," 9, pp. 1545-1551, (1973).

Primary Examiner—David Wheeler
Attorney, Agent, or Firm—Millen & White

[57] ABSTRACT

New quinolone derivatives of the Formula I

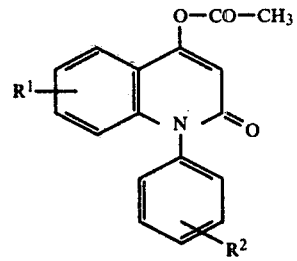

wherein $R^1$ and $R^2$ are each H, F, Cl, Br, CF$_3$ or CH$_3$O or a physiologically acceptable acid addition salt thereof possess pharmacological properties including thrombocyte aggregation inhibiting action.

9 Claims, No Drawings

QUINOLONE DERIVATIVES

SUMMARY OF THE INVENTION

An object of this invention is to provide new compounds which can be used for the preparation of medicaments.

Upon further study of the specification and appended claims, further objects and advantages of this invention will become apparent to those skilled in the art.

The objects of this invention have been achieved, in a composition aspect, by providing new quinolone derivatives of the Formula I

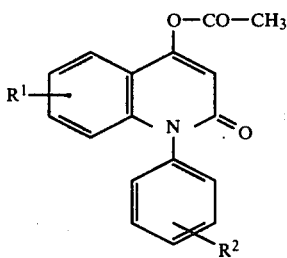

where $R^1$ and $R^2$ are each H, F, Cl, Br, $CF_3$ or $CH_3O$.

In a second composition aspect, this invention relates to a pharmaceutical composition comprising an amount of a compound of Formula I effective to inhibit thrombocyte aggregation and a pharmaceutically acceptable carrier.

In a method-of-use aspect, this invention relates to a method of inhibiting thrombocyte aggregation in mammals, including humans, which comprises administering an amount of a compound of Formula I effective to inhibit thrombocyte aggregation.

DETAILED DISCUSSION

In Formula I, $R^1$ is preferably H and also Cl. When $R^1$ is not H, it is preferably in the 6-position. However, it can also be in the 5-position, the 7-position or 8-position. $R^2$ is preferably H, Cl, $CF_3$ or $CH_3O$ and is preferably in the 4-position of the phenyl ring. However, it can also be in the 2- or 3-position.

This invention furthermore relates to processes for preparing the quinolone derivatives of Formula I. In one method, an anthranilic acid derivative of Formula II

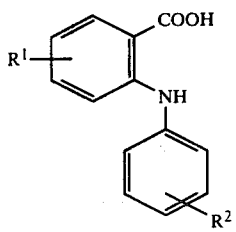

wherein $R^1$ and $R^2$ are as defined above, it reacted with acetic anhydride. Alternatively, a quinolone derivative of Formula III

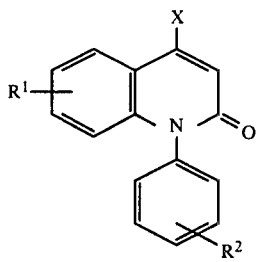

wherein X is OH or reactively functionally modified OH, in particular Cl, Br or I, can be reacted with acetic acid or a reactive derivative thereof.

In the Formula III starting materials, X is preferably OH, and also Cl, Br or I; alkylsulphonyloxy having 1-6 C atoms, for example, methanesulphonyloxy or arylsulphonyloxy having 6-10 C atoms, for example, benzenesulphonyloxy, p-toluenesulphonyloxy or 1- or 2-naphthalenesulphonyloxy.

The quinolone derivatives of Formula I are preferably obtained by reacting the anthranilic acid derivatives of Formula II with acetic anhydride. The starting materials of Formula II can be conventionally prepared, for example, by reacting the corresponding 2-halogenobenzoic acid, which has $R^1$ in its benzene ring, with the appropriate aniline derivative of the Formula $R^2$-$C_6H_4$-$NH_2$ in analogy to the method described by P. Caubere in Bull. Soc. Chim. France 1967, pages 3446 and 3451 and to another method described in Chemical Abstract 54, 24549 g (1960).

The reaction of a compound of Formula II with acetic anhydride can be carried out either with or without an additional solvent. In the latter case, an excess of acetic anhydride serves as the solvent. Suitable additional inert solvents include, in particular, carboxylic acids, such as acetic acid, and also halogenated hydrocarbons, such as chlorobenzene or bromobenzene, and hydrocarbons, such as toluene or xylene. The reaction is advantageously carried out at temperatures between about 0° and about 200° C., preferably between 110° and 150° C.

The starting materials of Formula III are obtainable, for example, by reacting diphenylamine derivatives of the Formula, $R^1$-$C_6H_4$-NH-$C_6H_4$-$R^2$, with malonic acid derivatives, for example, malonic acid monethyl ester monochloride; and subsequently cyclising the resulting malonic acid mono-di-phenylamide, for example with polyphosphoric acid in analogy to the method described in Organic Syntheses Coll. Vol. III, 798 (1955).

The resultant 4-hydroxyquinolone derivatives of Formula III (X=OH) can subsequently be converted into the coresponding 4-halogeno-quinolone derivatives by treating with halogen compounds, such as $POCl_3$, $PBr_3$ or HI in analogy to the method described by R. St. Tipson, J. org. Chem. 27, 1449 (1962), or into the corresponding sulphonic acid esters by esterification with the corresponding sulphonyl chlorides.

Suitable reactive derivatives of acetic acid include, for example, the corresponding salts, in particular the Cu-II salt, and also acetic anhydride, acetyl chloride or bromide and ketene. In other respects, the reaction is performed in analogy to methods which are completely conventional and which are described, for example, by P. Z. Bedoukian, J. Am. Chem. Soc. 67, 1430 (1945). The hydroxy-quinolone derivatives III (X=OH) are preferably acetylated with acetic anhydride, an acetyl halide or ketone. It is also possible for a base, such as triethylamine or pyridine, and/or one of the customary inert solvents, for example a hydrocarbon, such as benzene, to be present. Esterification of the 4-hydroxyquinolone derivative with acetic acid is preferably effected in the presence of a dehydrating agent, such as dicyclohexylcarbodiimide. The conversion of the 4-halogeno-quinolone derivatives and of the corresponding sulphonic acid esters is preferably effected with salts of acetic acid, preferably heavy metal salts, in particular cooper-II acetate, in solvents, such as phosphoric acid hexamethyltriamide or dimethylsulphoxide. These conversions are also preferably carried out at temperatures between about 0° and about 200° C., preferably between 50° and 130° C.

It has been found that the quinolone derivatives of Formula I possess valuable pharmological properties, coupled with good tolerance. They exhibit, in particular, thrombocyte aggregation inhibiting action, which can be demonstrated, for example, with the aid of the platelet aggregation test according to K. Breddin (Thrombos, Diathes, haemorrh. Supp. 27 (1968). Moreover, the influence on the trombocyte function, i.e., an inhibition of aggregation (adhesion), can also be demonstrated on rabbits in the Born test in vitro and ex vivo [method based on that given in Nature, Volume 194 (1962), pages 927–929] and in the fiber test according to Jacobi [method based on that given in Thrombos. Diathes, haemorrh. Volume 26 (1971), pages 192–202]. In addition, the compounds are also effective for lowering blood sugar and display antiphlogistic properties. These properties can be determined by conventional methods.

The quinolone derivatives of the Formula I can therefore be used as medicaments in human medicine and in veterinary medicine. Furthermore, they can also be used as intermediate products for the preparation of other medicaments.

The new compounds of Formula I can be used for the preparation of pharmaceutical formultions by bringing them into suitable dosage forms, together with at least one excipient or auxiliary and optionally together with one or more additional active compound(s). The formulation thus obtained can be employed as medicaments in human medicine or in veterinary medicine. Suitable excipients include organic or inorganic substances which are suitable for enteral or parenteral administration or topical application and with which the new compounds do not react, for example water, vegetable oils, benzyl alcohols, polyethylene glycols, gelatine, carbohydrates, such as lactose or starch, magnesium stearate, talc or petroleum jelly. Tablets, dragees, capsules, syrups, elixirs, drops or suppositories, in particular, are used for enteral administration; solutons, preferably oily or aqueous solutions, and also suspensions, emulsions or implantates are used for parenteral administration; and ointments, creams or powders are used for topical application. The new compounds can also be lyophilised and the resulting lyophilisates can be used, for example, for the preparation of injection formulations. The compositions mentioned can be sterilized and/or can contain auxiliaries, such as lubricants, preservatives, stabilizers and/or wetting agents, emulsifiers, salts for influencing the osmotic pressure, buffer substances, dyestuffs, flavoring agents and/or aroma generating substances. If desired, they can also contain one or more additional active compounds. As a rule, the substances of the invention can be administered analogously to known commercially available antithrombotic agents, such as acetylsalicylic acid, preferably in dosages between about 10 and 5,000 mg, in particular between 50 and 1,500 mg. per dosage unit. The daily dosage is preferably between about 0.2 and 80 mg/kg of body weight. However, the specific dose for each particular patient depends on the usual diversity of factors, for example, on the activity of the specific compound employed; on the age, body weight general state of health, sex and diet of the patient; on the time and path of administration; on the rate of excretion and the medicament combination; and on the severity of the particular illness to which the therapy applies. Oral administration is preferred.

Each of the compounds of the Formula I mentioned in the Examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A mixture of 243 g of 2-carboxyl-4'-methoxy-diphenylamine (m.p. 180°–182°; obtainable from 2-chlorobenzoic acid and p-anisidine in the presence of copper powder and potassium carbonate), 600 ml of acetic acid and 600 ml of acetic anhydride is boiled for 4 hours. The mixture is evaporated, the residue treated with 320 ml of ethanol and the mixture cooled. The 1-p-methoxyphenyl-4-acetoxy-1,2-di-hydroquinolin-2-one which precipitates is filtered off; m.p. 174°–175°.

Analogously, reacting 2-carboxydiphenylamine, 2-carboxy-2'-fluoro-diphenylamine, 2-carboxy-3'-fluoro-di-phenylamine, 2-carboxy-4'-fluoro-diphenylamine, 2-carboxy-2'-chloro-diphenylamine, 2-carboxy-3'-chloro-diphenylamine,-b 2-carboxy-4'-chloro-diphenylamine, 2-carboxy-2'-bromo-diphenylamine, 2-carboxy-3'-bromo-diphenylamine, 2-carboxy-4'-bromo-diphenylamine, 2-carboxy-2'-trifluoromethyl-diphenylamine, 2-carboxy-3'-trifluoromethyl-diphenylamine, 2-carboxy-4-trifluoromethyl-diphenylamine, 2-carboxy-2'-methoxy-diphenylamine, 2-carboxy-3'-methoxy-diphenylamine, 2-carboxy-6-fluoro-diphenylamine, 2-carboxy-5-chloro-diphenylamine, 2-carboxy-6-chloro-diphenylamine, 2-carboxy-7-chloro-diphenylamine, 2-carboxy-8-chloro-diphenylamine, 2-carboxy-6-bromo-diphenylamine, 2-carboxy-6-trifluoromethyl-diphenylamine, 2-carboxy-6-methoxy-diphenylamine, 2-carboxy-6-chloro-3'-trifluoromethyl-diphenylamine or 2-carboxy-6-chloro-4'-methoxy-diphenylamine with acetic anhydride/acetic acid gives 1-phenyl-4-acetoxy-1,2-dihydroquinolin-2-one,
1-o-fluorophenyl-4-acetoxy-1,2-dihydroquinolin-2-one,
1m4-acetoxy-1,2-dihydroquinolin-2-one,
1-p-fluorophenyl-4-acetoxy-1,2-dihydroquinolin-2-one,
1-o-chlorophenyl-4-acetoxy-1,2-dihydroquinoline-2-one,
1-m-chlorophenyl-4-acetoxy-1,2-dihydroquinolin-2-one,
1-p-chlorophenyl-4-acetoxy-1,2-dihydroquinolin-2-one, m.p. 173°–174°, 1-o-bromophenyl-4-acetoxy-1,2-dihydroquinolin-2-one,
1-m-bromophenyl-4-acetoxy-1,2-dihysroquinolin-2-one,
1-p-bromophenyl-4-acetoxy-1,2-dihydroquinolin-2-one,
1-o-trifluoromethylphenyl-4-acetoxy-1,2-dihydroquinolin-2-one, 1-m-trifluoromethylphenyl-4-acetoxy-1,2-dihydroquinolin-2-one, m.p. 135°–138°,
1-p-trifluoromethylphenyl-4-acetoxy-1,2-dihydroquinolin-2-one,
1-o-methyoxyphenyl-4-acetoxy-1,2-dihydroquinolin-2-one,
1-m-methoxyphenyl-4-acetoxy-1,2-dihydroquinolin-2-one,
1-phenyl-4-acetoxy-6-fluoro-1,2-dihydroquinolin-2-one,
1-phenyl-4-acetoxy-5-chloro-1,2-dihydroquinolin-2-one,
1-phenyl-4-acetoxy-6-chloro-1,2-dihydroquinolin-2-one,
1-phenyl-4-acetoxy-7-chloro-1,2-dihydoquinolin-2-one,
1-phenyl-4-acetoxy-8-chloro-1,2-dihydroquinolin-2-one,
1-phenyl-4-acetoxy-6-bromo-1,2-dihydroquinolin-2-one,
1-phenyl-4-acetoxy-6-trifluoromethyl-1,2-dihydroquinolin-2-one,
1-phenyl-4-acetoxy-6-methoxy-1,2-dihydroquinolin-2-one,
1-m-trifluoromethylphenyl-4-acetoxy-6-chloro-1,2-dihydroquinolin-2-one or
1-p-methoxyphenyl-4-acetoxy-6-chloro-1,2-dihydroquinolin-2-one.

EXAMPLE 2

A mixture of 28.55 g of 1-p-methoxyphenyl-4-chloro-1,2-dihydro-quinolin-2-one [m.p. 187°–190°; obtainable by reacting p-methoxydiphenylamine with malonic acid monoethyl ester monochloride to give N-carbethoxyacetyl-p-methyoxydiphenylamine, cyclising this with polyphosphoric acid, separating the cyclisation products by chromatography on silica gel and heating the resulting 1-p-methoxyphenyl-4-hydroxy-1,2-dihydroquinolin-2-one (m.p. about 300°) with POCl$_3$], 20 g of copper-II acetate and 400 ml of phosphoric acid hexamethyltriamide are heated to 100° for 12 hours. The reaction mixture is worked up with water and CH$_2$Cl$_2$ to give 1-p-methoxyphenyl-4-acetoxy-1,2-dihydro-quinolin-2-one, m.p. 174°–175°.

The examples which follow relate to pharmaceutical formulations which contain quinolone derivatives of the Formula Example A: Tablets A mixture of 1 kg of 1-p-methoxyphenyl-4-acetosy-1,2-dihydroquinolin-2-one, 4 kg of lactose, 1,2 kg of potato starch, 0.2 kg of talc and 0.1 kg of magnesium stearate is pressed with tablets in the customary manner such that each tablet contains 100 mg of active compound.

Example B: Dragees

Analogously to Example A, tablets are pressed and are subsequently coated in the customary manner with a coating of sucrose, potato starch, talc, tragacanth and a dyestuff.

Example C: Capsules 5 kg of 1-p-methoxyphenyl-4-acetoxy-1,2-dihydroquinolin-2-one are filled into hard gelatin capsules in the customary manner so that each capsule contains 250 mg of the active compound.

Tablets, dragees and capsules which contain one or more of the other active compounds of the Formula I can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. a pharmaceutical composition in table, capsule or dragee form which comprises, in admixture with a pharmaceutically acceptable adjuvant, an amount effective to inhibit thrombocyte aggregation of a compound of the formula

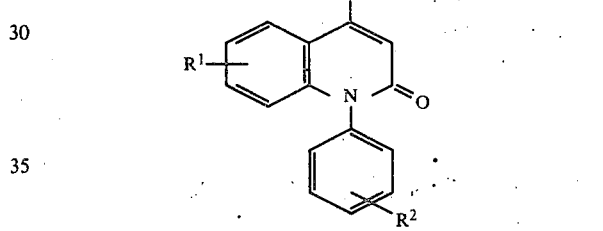

wherein $R^1$ and $R^2$ are each H, F, Cl, Br, CF$_3$ or CH$_3$O.

2. The composition of claim 1 wherein $R^1$ is H.

3. A composition of claim 1 wherein, $R^1$ is Cl in the 6-position.

4. The composition of claim 1 wherein $R^2$ is CH$_3$O.

5. The composition of claim 4 wherein $R^2$ is in the 4-position.

6. The composition of claim 1 wherein the compound therein is 1-p-methoxyphenyl-4-acetoxy-1,2-dihydroquinolin-2-one.

7. A compound selected from the group consisting of 1-o-methoxyphenyl-4-acetoxy-1,2-dihydro-quinoline-2-one; 1-m-methoxyphenyl-4-acetoxy-1,2-dihydroquinolin-2-one; 1-p-methoxyphenyl-4-acetoxy-1,2-dihydro-quinolin-2-one; 1-o-trifluoromethylphenyl-4-acetoxy-1,2-dihydro-quinolin-2-one; 1-m-trifluoromethylphenyl-4-acetoxy-1,2-dihydro-quinolin-2-one; 1-p-trifluoromethylphenyl-4-acetoxy-1,2-dihydro-quinolin-2-one; 1-m-trifluoromethylphenyl-4-acetoxy-6-chloro-1,2-dihydro-quinolin-2-one; and 1-p-methoxyphenyl-4-acetoxy-6-chloro-1,2-dihydro-quinolin-2-one.

8. 1-p-methoxyphenyl-4-acetoxy-1,2-dihydro-quinolin-2-one, a compound of claim 7.

9. A method of inhibiting thrombocyte aggregation in mammals which comprises administering systemically thereto an amount of a compound of the formula

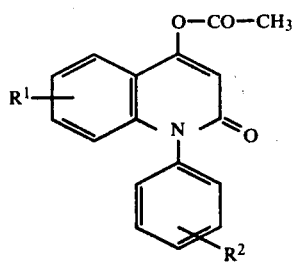
wherein $R^1$ and $R^2$ are each H, F, Cl, Br, $CF_3$ or $CH_3O$, effective to inhibit thrombocyte aggregation.
* * * * *